(12) United States Patent
Ullucci et al.

(10) Patent No.: US 8,003,810 B2
(45) Date of Patent: Aug. 23, 2011

(54) PROCESS FOR PREPARING NEBIVOLOL

(75) Inventors: Elio Ullucci, Latina (IT); Paolo Maragni, Virgilio (IT); Livius Cotarca, Cervignano del Friuli (IT); Johnny Foletto, Arcole (IT)

(73) Assignee: Zach System S.p.A., Bresso (IT)

( * ) Notice: Subject to any disclaimer, the term of this patent is extended or adjusted under 35 U.S.C. 154(b) by 51 days.

(21) Appl. No.: 12/515,581

(22) PCT Filed: Nov. 23, 2007

(86) PCT No.: PCT/EP2007/010184
§ 371 (c)(1),
(2), (4) Date: Jun. 30, 2009

(87) PCT Pub. No.: WO2008/064826
PCT Pub. Date: Jun. 5, 2008

(65) Prior Publication Data
US 2010/0076206 A1 Mar. 25, 2010

(30) Foreign Application Priority Data
Nov. 27, 2006 (EP) .................................... 06124838

(51) Int. Cl.
C07D 311/04 (2006.01)
C07D 407/04 (2006.01)
(52) U.S. Cl. ..................... 549/407; 549/398; 549/401
(58) Field of Classification Search .................. None
See application file for complete search history.

(56) References Cited

U.S. PATENT DOCUMENTS

| 5,665,890 A * | 9/1997 | Jacobsen et al. ............. 549/230 |
| 5,929,232 A | 7/1999 | Jacobsen et al. |
| 6,639,087 B2 | 10/2003 | Larrow et al. |
| 2003/0073855 A1 | 4/2003 | Liu et al. |

FOREIGN PATENT DOCUMENTS

| CN | 1649861 A | 8/2005 |
| WO | 2004/041805 A | 5/2004 |

OTHER PUBLICATIONS

Schaus, S. et al., "Highly selective hydrolytic kinetic resolution of terminal epoxides catalyzed by chiral (salen)Coiii complexes. Practical Synthesis of enantioenriched terminal epoxides and 1,2-diols" 2002, J. Am. Chem. Soc., vol. 124, No. 7, 1307-1315.
Bartoli, G. et al., "Asymmetric catalytic synthesis of enantiopure N-protected 1,2-amino alcohols" 2004, Organic Letters, vol. 6, No. 22, 3973-3975.
Tokunaga, M. et al., "Asymmetric catalysis with water: Efficient kinetic resolution of terminal epoxides by means of catalytic hydrolysis" 1997, Science, vol. 277, 936-938.

Nielsen, L. et al., "Mechanistic investigation leads to a synthetic improvement in the hydrolytic kinetic resolution of terminal epoxides" 2004, J. Am. Chem. Soc., vol. 126, 1360-1362.
White, D. et al. "New oligomeric catalyst for the hydrolytic kinetic resolution of terminal epoxides under solvent-free conditions" 2003, Tetrahedron: Asymmetry 14, 3633-3638.
Keith, J. et al. "Practical considerations in kinetic resolution reactions" 2001, Adv. Synth. Catal., vol. 343, No. 1, 5-26.
Ready, J. et al., "Asymmetric catalytic synthesis of alpha-aryloxy alcohols: Kinetic resolution of terminal epoxides via highly enantioselective ring-opening with phenols" 1999, J. Am. Chem. Soc., 121, 6086-6087.
Bartoli, G. et al., "Direct catalytic synthesis of enatiopure 5-substituted oxazolidinones from racemic terminal epoxides" 2005, Organic Letters, vol. 7, No. 10, 1983-1985.
Jacobsen, Asymmetric catalysis of epoxide ring-opening reactions, Accounts of Chemical Research, 2000, 33 (6):421-431.
Chandrasekhar, et al., Enantioselective total synthesis of the antihypertensive agent (S,R,R,R)-nebivolol, Tetrahedron, 2000, 56:6339-6344.
Yu, et al., A Convenient Synthesis of 1-[6-Fluoro-(2S)-3H,4H-1-dihydro-2H-2-chromenyl]-. (1R)-1,2-ethanediol and 1-[6-Fluoro-(2R)-3H,4H-dihydro- 2H-2-chromenyl]-. (1R)-1,2-ethanediol, Synlett, 2005, 9:1465-1467.
Johannes, et al., Zr-catalyzed kinetic resolution of allylic ethers and Mo-catalyzed chromene formation in synthesis. Enantioselective total synthesis of the antihypertensive agent (S,R,R,R)-nebivolol, J. Am. Chem. Soc., 1998, 120 (33):8340-8347.
Yang, et al., Synthesis and resolution research of (R)- and (S)-6-fluorochroman-2-carboxylic acids, Chinese Journal of Organic Chemistry, 2005, 25(2):201-203.
Submission of Third Parties Observations pursuant to Article 115 EPC in connection with European Application No. 07846784.2, dated Mar. 30, 2010.
Zhang Qingshan Li Aiying, "Graphical synthetic routes of (S,R,R,R)-nebivolol." Chinese Journal of Pharmaceuticals, vol. 34, No. 7, pp. 366-367 and English Translation thereof. (2003).
Chinese Office Action dated Mar. 14, 2011 (and English Translation thereof), issued in counterpart Chinese Application No. 200780043750.5.

* cited by examiner

*Primary Examiner* — Bernard Dentz
(74) *Attorney, Agent, or Firm* — Lucas & Mercanti, LLP

(57) ABSTRACT

The present invention relates to a process for preparing Nebivolol and, more particularly, to an improved process for synthesizing enantiomerically enriched 6-fluoro chroman alcohol or epoxide derivatives of formula, wherein R and X is defined in the description; as useful intermediates in the preparation of Nebivolol.

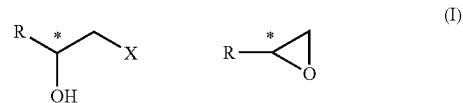

(I)

27 Claims, No Drawings

PROCESS FOR PREPARING NEBIVOLOL

This application is a 371 of PCT/EP2007/010184 filed on Nov. 23, 2007, which claims the benefit of European Patent Application No. 06124838.1 filed on Nov. 27, 2006, the contents of each of which are incorporated herein by reference.

The present invention relates to a process for preparing Nebivolol and, more particularly, to an improved process for synthesizing enantiomerically enriched 6-fluoro chroman alcohol or epoxide derivatives of formula

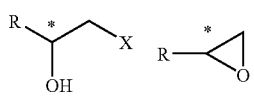

wherein R and X is hereinafter defined; as useful intermediates in the preparation of Nebivolol.

Nebivolol (hereinafter also referred to as NBV), is a mixture of equal amounts of [2S[2R*[R[R*]]]]α,α'-[imino-bis(methylene)]bis[6-fluoro-chroman-2-methanol] (hereinafter also referred to as d-NBV) of formula (IA)

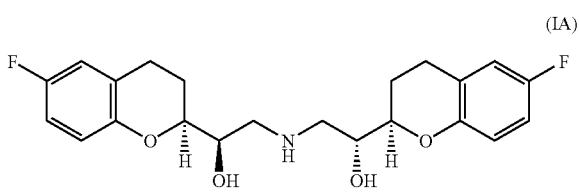

and its [2R[2S*[S[S*]]]] enantiomer (hereinafter also referred to as l-NBV) of formula (IB)

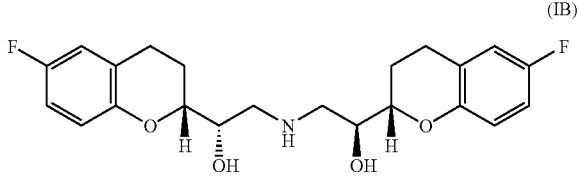

Nebivolol is characterized by β-adrenergic blocking properties and is useful for the treatment of essential hypertension. It has basic properties and may be converted into its pharmaceutically acceptable acid addition salt forms by treatment with appropriate acids. The hydrochloride acid addition salt is the marketed product.

It is well understood in the art that the synthesis of α,α'-[imino-bis(methylene)]bis[chroman-2-methanol] molecular structures is challenging for the skilled person, because of the 4 asymmetric carbon atoms producing a mixture of 16 stereoisomers (in case of asymmetrical substitution) or a mixture of 10 stereoisomers (in case of symmetrical substitution). As apparent from the presence of the topological symmetry in the structure of the α,α'-[imino-bis(methylene)]bis[6-fluoro-chroman-2-methanol], the following 10 stereoisomers can be generated.

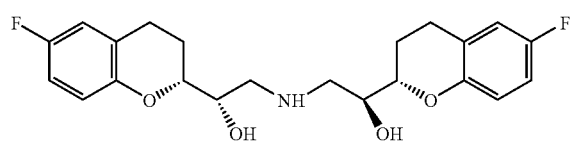
L-(R, S, S, S)-Nebivolol

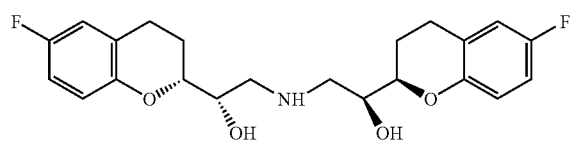
(R, S, S, R)-Nebivolol

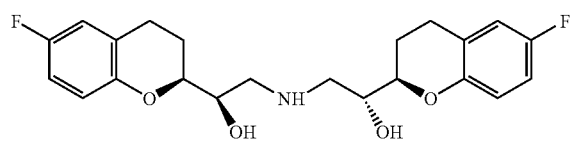
D-(S, R, R, R)-Nebivolol

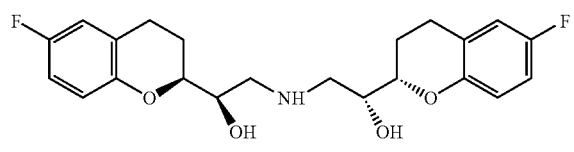
(S, R, R, S)-Nebivolol

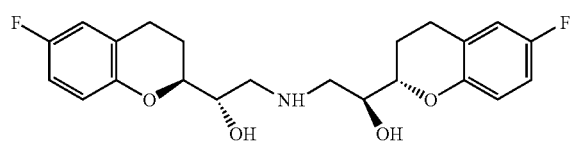
(S, S, S, S)-Nebivolol

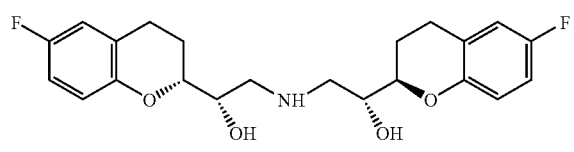
(R, S, R, R)-Nebivolol

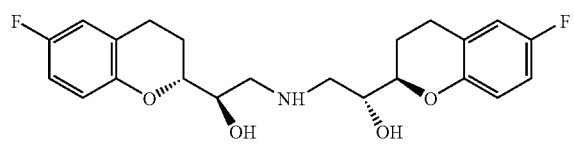
(R, R, R, R)-Nebivolol

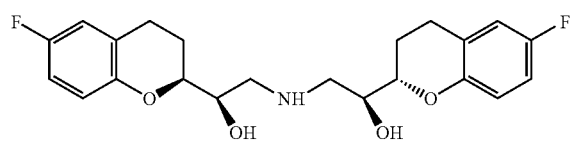
(S, R, S, S)-Nebivolol

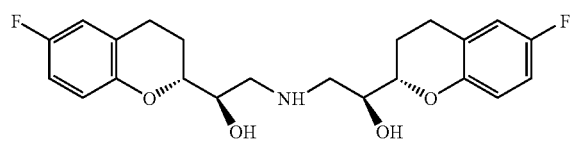
(R, R, S, S)-Msso 2

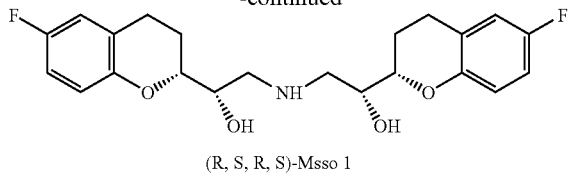

(R, S, R, S)-Msso 1

The European patent application EP 145067 describes methods for the preparation of substituted α,α'-[imino-bis(methylene)]bis[chroman-2-methanol] including the 6,6' bis-fluoro derivatives, which comprises reducing chroman-2-carboxylic acid into the corresponding aldehyde and then transforming the aldehyde into the corresponding epoxide as a mixture of four (R,S), (S,R), (RR) and (SS) stereoisomers. Epoxide stereoisomers are separated by column chromatography into racemic (R,S) and (S,R) epoxide (hereinafter mixture A) and racemic (R,R) and (S,S) epoxide (hereinafter mixture B), which represent the key intermediates of the process.

Mixture A (R,S;S,R) or, alternatively, mixture B (R,R;S,S) is treated with benzyl amine to give the racemic benzylated product, which is subsequently reacted with mixture B (R,R;S,S) or mixture A (R,S;S,R), respectively, to give a racemic mixture comprising four of the possible isomers of benzylated Nebivolol in accordance with the following synthetic scheme:

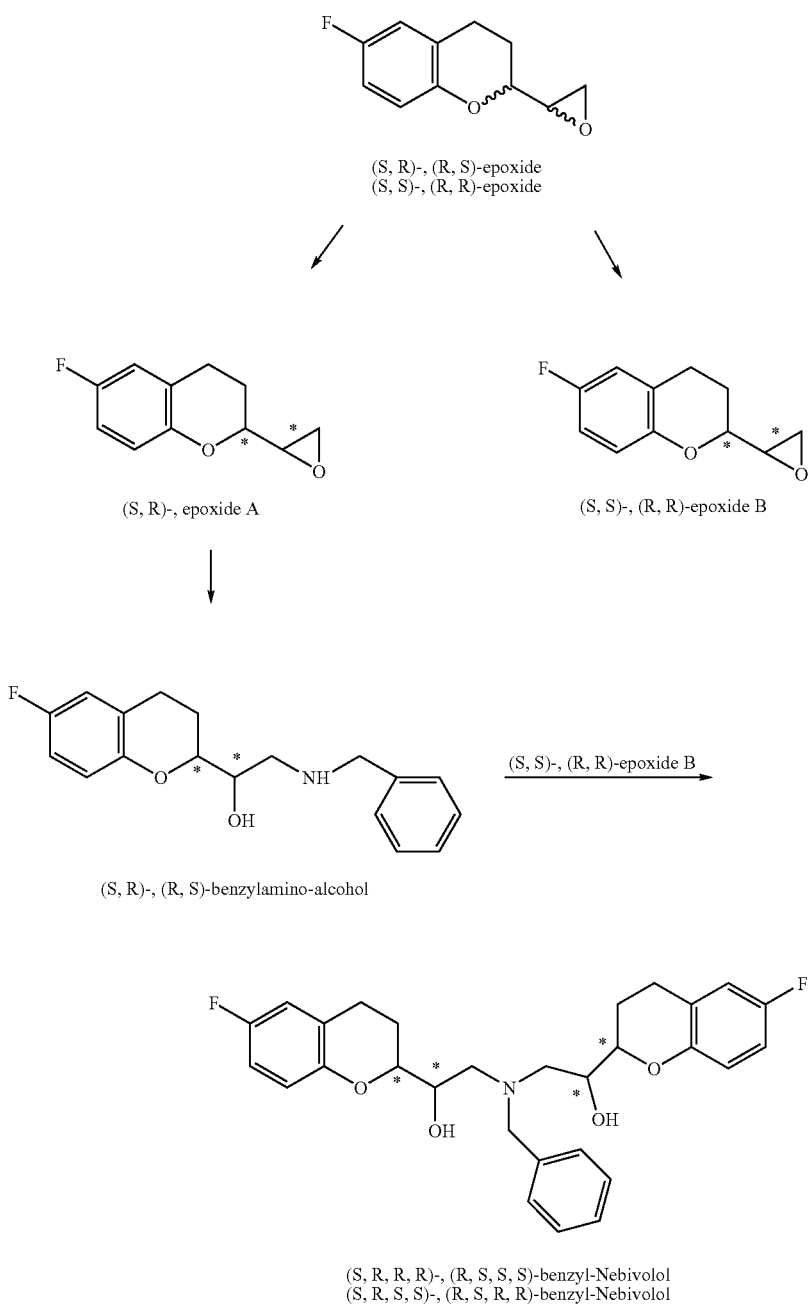

The above Nebivolol racemic mixture can be separated by chromatography to give the desired diastereomer as a pair of enantiomers (R,S,S,S;S,R,R,R) which are debenzylated to give pure Nebivolol (racemate).

Alternatively, the racemic mixture of four isomers of benzyl-Nebivolol can be debenzylated and, according to U.S. Pat. No. 5,759,580, the pure Nebivolol (R,S,S,S;S,R,R,R) is separated from the undesired diastereoisomers (R,S,R,R;S,R,S,S) by crystallizing the former as an hydrochloride salt.

Nevertheless, both these procedures show, as main drawback, the lost of, at least, 50 wt % of the material. In fact, during the chromatographic separation or the crystallization the two undesired diastereoisomers, which are present in equal amount compared to Nebivolol, are wasted.

The European patent application EP 334429 describes a process for the preparation of Nebivolol which comprises the resolution of 6-fluoro-chroman-carboxylic acid by using (+)-dehydroabiethylamine, the conversion of single enantiomers into two separated mixture of diastereoisomeric epoxides and the separation of the so obtained mixtures into four enantiomerically pure epoxides which are favourably combined to give l-NBV and d-NBV. Nevertheless, the above synthetic process suffers of some significant drawbacks: resolution reaction of chroman-carboxylic acid is not easy and it requires many procedural steps such as acyl chloride formation, amidation, hydrolysis, etc.; resolving agent is expensive and is used in stechiometric amount; yields are very low, respectively 11.3% for (+)-(S)-chroman-carboxylic acid and 9.2% for (−)-(R)-chroman-carboxylic acid; transformation of carboxylic acid to epoxide is carried out at very low temperatures and it requires special precautions to avoid racemization; the whole process involves a very large number of steps thereby requiring increased costs on manufacturing scale in terms of utilities, manpower and time required to complete the production cycle.

The existence of the 4 stereogenic centres moved the skilled person towards the exploration of stereoselective methods for preparing the l-NBV and the d-NBV. For example, Johannes C. W. et al. (J. Am. Chem. Soc., 120, 8340-8347, 1998) and Chandrasekhar S. et al. (Tetrahedron 56, 6339-6344, 2000) describe enantioselective total preparations of d-NBV; An-Guang Yu et al. (Synlett, 9, 1465-1467, 2005) illustrate a method for the construction of chiral chroman intermediates, and Yang Yun-Xu et al. (Chinese Journal of Organic Chemistry, 25(2), 201-203, 2005 and the Chinese patent application CN 1629154) show the synthesis and resolution of (R) and (S) 6-fluorochroman carboxylic acids intermediates useful for the synthesis of d-NBV and l-NBV.

Additional alternative total synthetic approaches for the preparation of NBV can be found in the following international patent applications: WO 2004/041805, WO 2006/016376 and WO 2006/025070.

It is known in the art the key role of 6-fluoro-chroman epoxide derivatives in the preparation of NBV.

It results still more critical the function of said epoxides in enantiomerically pure form in light of specific stereochemistry of the pharmaceutically active ingredient and loss in yields in desired racemic product NBV due to resolution reactions in the final steps of classic preparation.

Thus, it would be desirable to study alternative methods for the preparation of enantiomerically enriched epoxides or direct precursors thereof which allow to overcome the drawbacks of the process described in the art.

We have now surprisingly found an easy and efficient synthesis of key intermediates useful in the preparation of l-NBV and d-NBV, via an hydrolytic or aminolytic kinetic resolution carried out on 6-fluoro-chroman racemic terminal epoxide derivatives.

It is therefore a first object of the present invention a process for the separation of racemic terminal epoxide of formula

wherein R is a group of formula

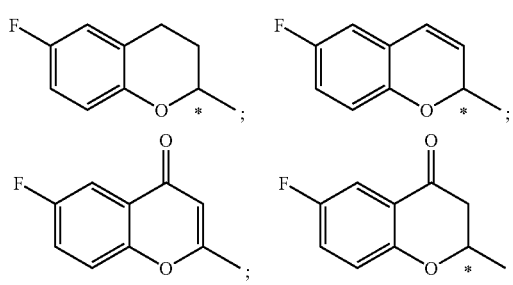

to give an enantiomerically enriched substituted alcohol of formula

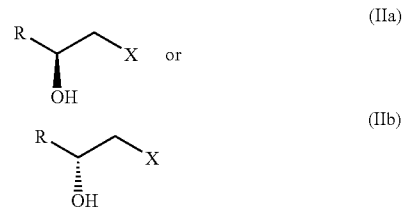

wherein X is hydroxy or amino group;
and, respectively, an enantiomerically enriched epoxide of formula

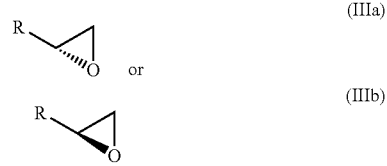

which comprises a hydrolytic or aminolytic kinetic resolution carried out in the presence of a non-racemic transition metal-ligand catalyst complex.

The racemic terminal epoxides of formula I are intermediates in the preparation of NBV and they are obtained in accordance with known methods. Some synthetic processes for the preparation of the above substrates of the present invention are described in the following documents: EP 0331078, U.S. Pat. No. 4,654,362, WO 2004/041805, Synlett 2005, 9, pages 1465-1467. A compound of formula Ia wherein R is a 6-fluoro-3,4-dihydro-1-benzopyran group is prepared according to the above cited EP 145067. 4-fluorophenol is reacted with dimethyl acetylenedicarboxylate to give a phenoxy-ethylene compound of formula

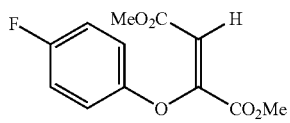
IV which is hydrolysed in alkali media; so obtained dicarboxylic acid derivative is reacted with sulphuric acid to give a compound of formula

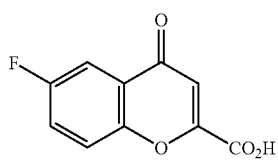
V which is converted by catalytic hydrogenation into a compound of formula

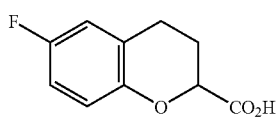
VI racemic 6-fluoro-chroman-carboxylic acid (VI) is treated with 1,1'-carbonyldiimidazole and is reduced with diisobutylaluminum hydride into a compound of formula

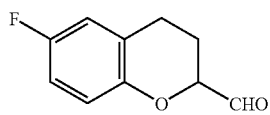
VII which is reacted with sodium hydride and trimethyl sulfoxonium iodide to give the corresponding epoxide as a mixture of four (R,S), (S,R), (R,R), and (S,S) stereoisomers of formula

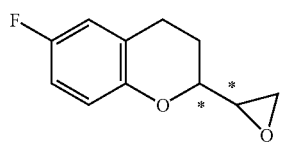
Ia

A compound of formula Ib wherein R is a 6-fluoro-4-oxo-4H-1-benzopyran group is prepared by the following procedure. A compound of formula V is treated with 1,1'-carbonyldiimidazole and is reduced with diisobutylaluminum hydride to give a compound of formula

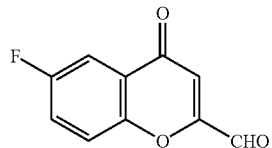
VIII which is reacted with sodium hydride and trimethyl sulfoxonium iodide into the corresponding racemic epoxide of formula

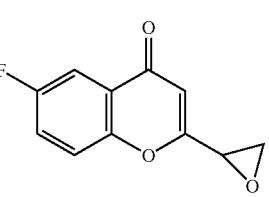
Ib

A compound of formula Ic wherein R is a 6-fluoro-4-oxo-1-benzopyran group is prepared by the following procedure. 5'-fluoro-2'-hydroxyacetophenone is reacted with racemic 2,2-dimethyl-1,3-dioxane-4-carbaldehyde in alkali media to obtain a mixture of stereoisomers of formula

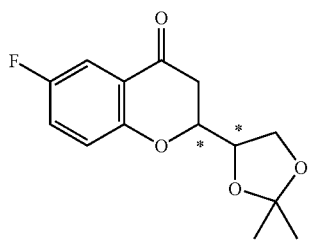
IX which is treated in acid media; so obtained diol is reacted with p-TsCl into the corresponding tosylated compound of formula

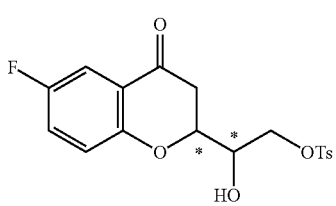
X which is treated in alkali media to obtain the corresponding epoxide as a mixture of four (R,S), (S,R), (R,R), and (S,S) stereoisomers of formula

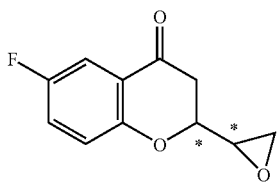

Ic

A compound of formula Id wherein R is a 6-fluoro chromen-2-yl group is prepared by the following procedure. 2,2-dimethyl-1,3-dioxane-4-carbaldehyde is reacted with vinyl Grignard reagent to obtain a mixture of stereoisomers of formula

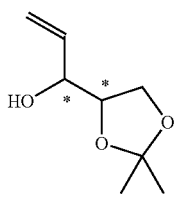

XI which is reacted with 2-bromo-4-fluorophenol or 2-bromo-4-fluorophenyl acetate by palladium catalyst to obtain a mixture of stereoisomers of formula

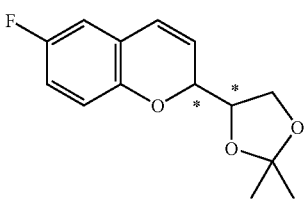

XII which is treated according to procedure used for compound IX to obtain corresponding epoxide as a mixture of four (R,S), (S,R), (R,R), and (S,S) stereoisomers of formula

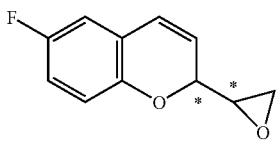

Id

Hydrolytic kinetic resolutions of terminal epoxides catalyzed by chiral catalyst complexes are well known in the art. Examples of kinetic resolution of cyclic substrates such as epoxides in U.S. Pat. No. 5,665,890, U.S. Pat. No. 5,929,232, U.S. Pat. No. 5,663,393, U.S. Pat. No. 6,262,278 and US 2003/073855 are described.

The hydrolytic or aminolytic kinetic resolution of the invention comprises contacting a nucleophile and a racemic or diastereoisomeric mixture of a compound of formula I in the presence of a non-racemic transition metal-ligand catalyst complex.

In particular, the kinetic resolution comprises:
a) dissolution of a catalyst complex in a suitable aprotic or protic solvent;
b) activation of a catalyst complex by reaction with a suitable oxidizing agent in the presence of an organic or inorganic acid;
c) contacting the active catalyst complex with a racemic or diastereoisomeric mixture of a compound of formula I and a suitable nucleophile; and
(d) filtrating the reaction mixture.

Alternatively, the kinetic resolution comprises the activation of the catalyst in the presence of the terminal epoxide in accordance with the following steps:
a') contacting an oxidizing agent with a mixture comprising a racemic or diastereoisomeric compound of formula I, a non racemic catalyst complex, an organic or inorganic acid and a suitable nucleophile; and
b') filtrating the reaction mixture.

Suitable aprotic solvent useful in the dissolution step are toluene, dichloro methane, chloroform and the like.

Suitable protic solvent useful in the dissolution step are alcohols, preferably, methanol, ethanol and the like.

Preferred oxidizing agent is oxygen, more preferably, introduced in the form of air.

Suitable acid useful to prepare the active catalyst complex are Bronsted acids. Preferably, in the activation process of the invention organic Bronsted acids are used. More preferably, aryl or alkyl carboxylic acid such as acetic, propionic, isobutyrric, fluoroacetic, benzoic, nitro benzoic, fluoro benzoic, chloro benzoic and cyano benzoic acids are used. Still more preferably, acetic, benzoic and nitrobenzoic acids are used.

In contacting step, the active catalyst complex can be used directly as a solution or in solid form after precipitation.

Contacting step can be carried out at a temperature comprised between about −10° C. and about 50° C. Preferably, contacting step is carried out at around room temperature.

Generally the resolution takes place in around 1 to 48 hours, preferably, overnight.

Step d/b', filtration, allows to separate an enantiomerically enriched substituted alcohol of formula IIa or IIb, which precipitates from the reaction mixture, from an enantiomerically enriched epoxide of formula IIIa or IIIb, which remains in the mother liquor. Said epoxide of formula IIIa or IIIb can be, optionally, isolated as benzyl-amino alcohol derivative in accordance with known techniques.

The hydrolytic or aminolytic kinetic resolution of the invention can be run with or without addition of solvents.

Generally the reaction is carried out in ethers, alcohols, aromatic or aliphatic solvents, halogenated solvents or mixture thereof.

Preferred solvents are tert-butyl methyl ether, isopropyl alcohol, toluene, heptane, dichloromethane and the like.

In general, any compound having a reactive pair of electrons and able to join an oxygen or nitrogen atom to the substrate of formula I, is suitable as nucleophile of the kinetic resolution of the invention.

In particular, suitable nucleophiles according to the invention are oxygen nucleophiles such as water, hydroxide, alcohols, alkoxides, carboxylates or peroxides and nitrogen nucleophile such as azide, imide, ammonia, hydrazine, carbamate or amine.

Said nucleophiles are used to introduce an oxygen or nitrogen atom in the stereoselective epoxide opening reaction to give a compound of formula IIa or IIb wherein X is above defined.

In one embodiment of the invention, the kinetic resolution is carried out in the presence of suitable nucleophile able to directly give a compound of formula IIa or IIb wherein X is hydroxy or an amino group.

The skilled person will realize that the reaction of terminal epoxide according to the invention with further nucleophiles can yield functionalized compounds which are easily converted to useful intermediates in the NBV preparation wherein residue X is hydroxy or amino group, in accordance with known techniques.

Preferred oxygen nucleophiles are water, hydroxide and carboxylates such as acetate, benzoate, formate, chloroformate and the like.

Preferred nitrogen nucleophiles are carbamate, azide such as sodium azide or trimethylsilyl azide, imide such as phthalimide or succinimide and the like.

More preferred nucleophiles according to the invention are water and carbamate, in particular, a ($C_1$-$C_4$)-alkyl or benzyl carbamate.

Water and benzyl carbamate are the still more preferred ones.

Non-racemic metal complex catalysts according to the invention are composed of a large organic ligand complexed to a transition metal atom.

Generally, organic ligand are asymmetric tetradentate or tridentate ligand complexed with a metal atom.

Preferably, chiral salen or salen-like ligands are used in the process of the invention.

Particularly preferred are salen ligands disclosed in the above mentioned U.S. Pat. No. 5,665,890, U.S. Pat. No. 5,929,232, U.S. Pat. No. 5,663,393 and U.S. Pat. No. 6,262,278.

In a preferred embodiment the transition metal is selected from Mn, Cr, V, Fe, Co, Mo, W, Ru and Ni.

Preferably, the transition metal is Co or Cr, the former being the more preferred one.

Preferred non-racemic Co(II) complex catalysts are the (S,S)—Co(II) (salen) catalyst and (R,R)—Co(II) (salen) catalyst, respectively, represented by formulae

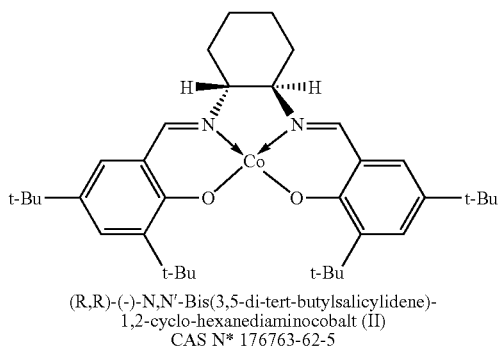

(R,R)-(-)-N,N'-Bis(3,5-di-tert-butylsalicylidene)-
1,2-cyclo-hexanediaminocobalt (II)
CAS N* 176763-62-5

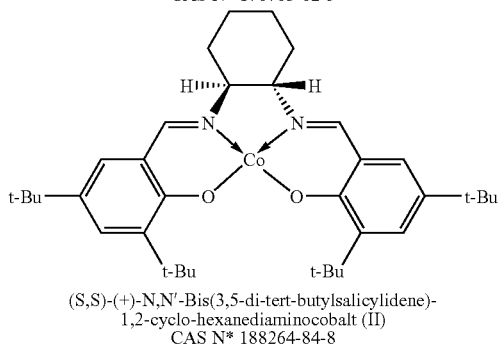

(S,S)-(+)-N,N'-Bis(3,5-di-tert-butylsalicylidene)-
1,2-cyclo-hexanediaminocobalt (II)
CAS N* 188264-84-8

In an embodiment of the invention (salen) Co(II) complex catalyst is readily converted to the desired active (salen) Co(III) catalyst having a carboxylate counter-anion by exposing to air and in the presence of an organic acid.

Preferred organic acids are acetic acid, benzoic acid and p-nitro-benzoic acid.

Alternatively, active Co (III) catalyst isolated by precipitation is directly used in the kinetic resolution of the invention.

Preferred non-racemic Co(III) complex catalysts are (S,S)—Co(III)(salen)(p-nitro-benzoate), (R,R)—Co(M)(salen)(p-nitro-benzoate), (S,S)—Co(III)(salen)(acetate) and (R,R)—Co(III)(salen)(acetate).

The catalyst complex is present in an amount comprised from 0.01 to 10 mol % with regard to a compound of formula I, preferably from 0.01 to 5 mol % and from 0.05 to 1 mol % representing the more preferred embodiment of the invention.

In a preferred embodiment of the invention, the kinetic resolution comprises the step of contacting oxygen with a mixture of a racemic terminal epoxides of formula I, a non-racemic Co(II) complex catalyst, an aryl or alkyl carboxylic acid and water or a suitable carbamate of formula $H_2NCOOR$ wherein R is defined above, at a temperature and for a time sufficient to produce a mixture of the enantiomerically enriched 2-substituted alcohols of formula II and correspondent enantiomerically enriched epoxides of the formula III.

Alternatively, said racemic terminal epoxides of formula I are contacted with water or a suitable carbamate of formula $H_2NCOOR$ wherein R is defined above in the presence of an active non racemic complex of Co(III) having an aryl or alkyl carboxylate counterion.

At the end of the resolution process the enantiomerically enriched 2-substituted alcohols of formula II is isolated by filtration and correspondent enantiomerically enriched epoxides of formula III is recovered in the mother liquor.

It is another object of the present invention a process for the separation of racemic terminal epoxide of formula

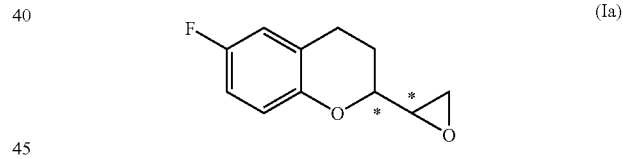

to give an enantiomerically enriched substituted alcohol of formula

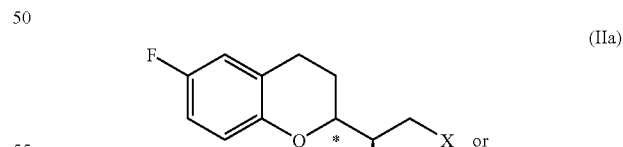

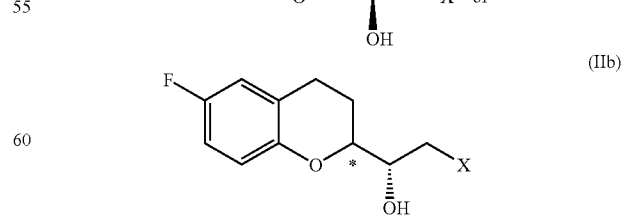

wherein X is defined above;
and, respectively, an enantiomerically enriched epoxide of formula

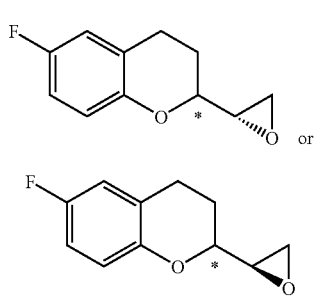 (IIIa)

or (IIIb)

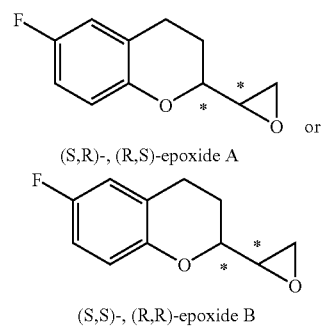
(S,R)-, (R,S)-epoxide A or (S,S)-, (R,R)-epoxide B which comprises a hydrolytic or aminolytic kinetic resolution carried out in the presence of a non-racemic transition metal-ligand catalyst complex.

The process according to the invention is directed to kinetic resolution of racemic or diastereoisomeric mixture of 6-fluoro chroman terminal epoxides and derivatives thereof. Thus, it is evident to the skilled person that the process of the invention can be applied to partially resolved compounds of formula Ia.

In one embodiment of the invention the kinetic resolution is carried out on partially resolved compounds of formula Ia

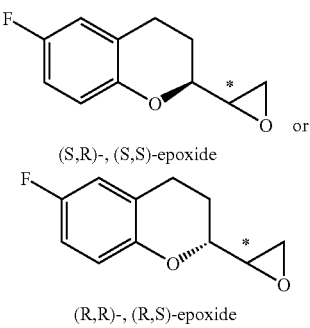
(S,R)-, (S,S)-epoxide or (R,R)-, (R,S)-epoxide in the form of diastereoisomeric mixtures prepared according to known methods such as those reported in the above cited EP334429 documents.

In a preferred embodiment of the invention the kinetic resolution is carried out on partially resolved compounds of formula Ia in the form of racemic mixtures (mixture A or mixture B).

The two racemic mixtures are obtained according to known techniques, in particular by chromatography in accordance with the above cited EP145067 documents.

It is another object of the present invention a process for the separation of racemic terminal epoxide of formula Ia further comprising the partial resolution of the four stereoisomers of formula Ia into mixture A and mixture B.

Thus, a mixture of four epoxides stereoisomers of formula Ia is separated, for instance by chromatography, to obtain two epoxides diastereoisomers each of them being a racemic mixture e.g. epoxide A as a mixture of (R,S) and (S,R) enantiomers (mixture A) and epoxide B as a mixture of (R,R) and (S,S) enantiomers (mixture B).

Preferably, the two epoxides A and B, (R,S;S,R) racemate and (R,R;S,S) racemate are separately contacted with, alternatively:

(a) a non-racemic Co (II) complex catalyst, an aryl or alkyl carboxylic acid and water or benzyl carbamate in the presence of oxygen;

(b) water or benzyl carbamate in the presence of a non-racemic complex of Co (III) having an aryl or alkyl carboxylate counter-anion;

wherein the contacting is carried out at a temperature and for a time sufficient to produce a mixture of the enantiomerically enriched 2-substituted alcohol of formula IIa or IIb (diol or carbamate) and of correspondent enantiomerically enriched epoxide of formula IIIa or IIIb in accordance with the following synthetic scheme

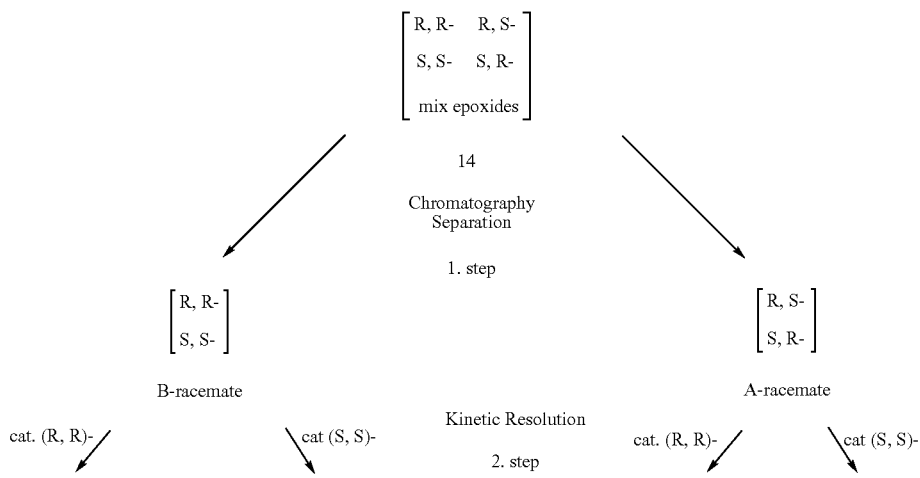

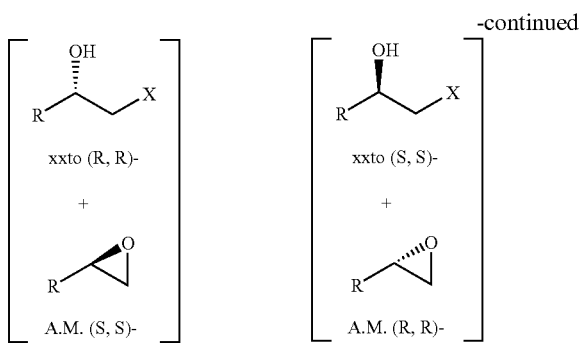

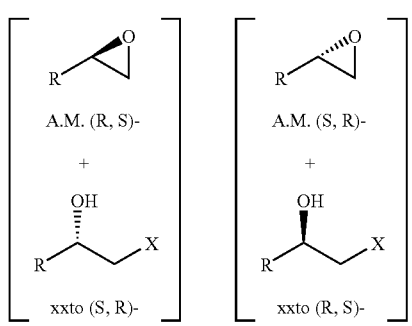

wherein X and R are defined above

As above reported, the enantiomerically enriched 2-substituted alcohols of formula II is isolated by filtration (xxto) and correspondent enantiomerically enriched epoxides of the formula III is recovered in the mother liquors (A.M.) or, optionally, converted in correspondent benzyl-amino alcohol derivative in accordance with known techniques.

The present invention further provides a process for producing Nebivolol by a kinetic resolution of key terminal epoxide intermediates of formula I.

It is another object of the present invention a process for preparing NBV which comprises the separation of racemic terminal epoxide of formula

wherein R is a group of formula

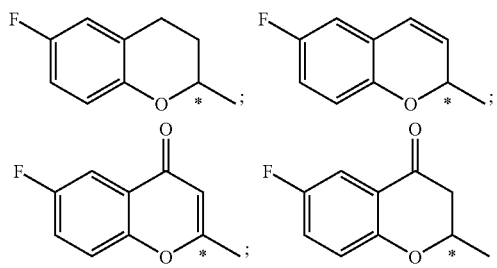

to give an enantiomerically enriched substituted alcohol of formula

wherein X is hydroxy or amino group;
and, respectively, an enantiomerically enriched epoxide of formula

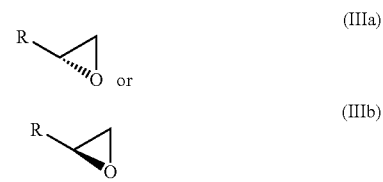

which comprises a hydrolytic or aminolytic kinetic resolution carried out in the presence of a non-racemic transition metal-ligand catalyst complex.

Optionally, a compound of formula IIa or IIb wherein X derives from a suitable oxygen nucleophile of the invention, is converted in a compound of formula IIa or IIb wherein X is a hydroxy group according to known techniques.

An enantiomerically enriched diol of formula IIa or IIb is, in turn, easily transformed into correspondent epoxide wherein stereochemistry is maintained according to known techniques. For example, a diol of formula IIa or IIb can be subjected to a tosylating reaction and then reacted with a base to give the desired epoxide compound.

Thus, starting from enantiomerically enriched epoxides is possible to obtain l-NBV and d-NBV by favourably combine single stereoisomers in accordance with known methods.

So, the compounds of formula IIa or IIb and, respectively, IIIa or IIIb wherein R is a 6-fluoro-4-oxo-1-benzopyran group are converted in l-NBV and d-NBV in accordance with what is disclosed in WO 2004/041805.

In a preferred embodiment of the invention, the enantiomerically enriched (R,R)-diol of formula II or a precursor thereof, isolated by filtration from the reaction mixture produced by contacting non racemic (R,R)—Co catalyst with epoxide racemate B (R,R;S,S) and optionally hydrolysed to give diol derivative, is tosylated to the corresponding (R,R)-tosylate; subsequently, the (R,R)-tosylate is converted into the corresponding (R,R)-epoxide of formula III in accordance with the following scheme

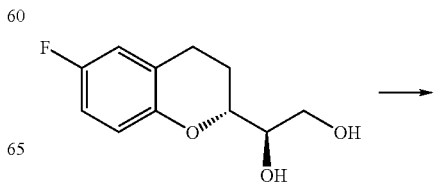

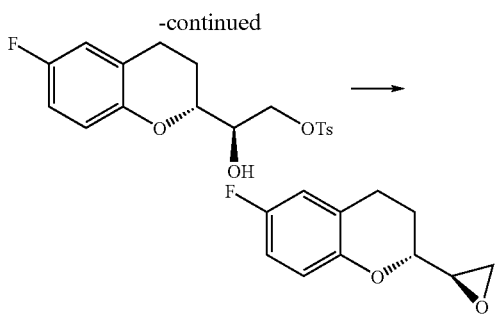

The enantiomerically enriched (S,R)-epoxide of formula III, recovered from mother liquor of the reaction mixture produced by contacting non racemic (S,S)—Co catalyst with epoxide racemate A (R,S;S,R), is reacted with benzyl amine to give the corresponding (S,R)-benzylamino-alcohol in accordance with the following scheme

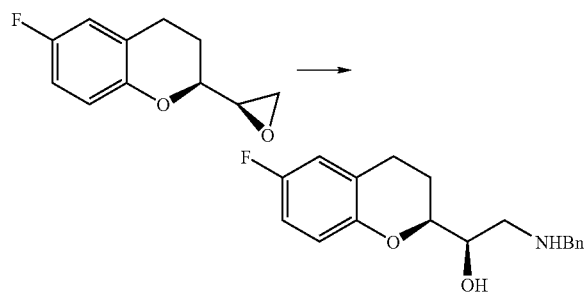

The (S,R)-benzylamino-alcohol is reacted with (R,R)-epoxide of the formula III to give (S,R,R,R)-benzyl Nebivolol; which is, in turn, debenzylated by catalytic hydrogenation to obtain d-NBV.

On the other side, the enantiomerically enriched (S,S)-epoxide of formula III is converted into the corresponding (S,S)-benzylamino-alcohol which is then reacted with the (R,S)-epoxide obtained from the enantiomerically enriched (R,S)-diol of formula II, to give (R,S,S,S)-benzyl Nebivolol. The latter is debenzylated by catalytic hydrogenation to obtain l-NBV.

The above described sequence of operations represents only one of the possible combinations by which it is possible to prepare the desired l-NBV and d-NBV.

For example, if non racemic (S,S)—Co catalyst is applied in the kinetic resolution on epoxide racemate B (R,R;S,S), and non racemic (R,R)—Co catalyst is applied on epoxide racemate A (R,S;S,R), we obtain, as a result, that the coupling procedure is carried out between the correspondent chiral intermediates derived from the enantiomerically enriched (S,S)-diol of formula II and the (R,S)-epoxide of formula III to give (R,S,S,S) Nebivolol (l-NBV) and, between the corresponding chiral intermediates derived from the enantiomerically enriched (S,R)-diol of formula II and the (R,R)-epoxide of formula III to give (S,R,R,R) Nebivolol (d-NBV)

The above reported procedures are not limiting the scope of invention, the skilled person will realize that other combinations of epoxides and substituted alcohols are still possible and do not depart from the spirit of the invention.

Alternatively, a compound of formula IIa or IIb wherein X derives from a suitable nitrogen nucleophile of the invention, is optionally converted in a compound of formula IIa or IIb wherein X is an amino group according to known techniques.

Thus, an enantiomerically enriched amino alcohol of formula IIa or IIb is, in turn, favourably combined with the correspondent suitable enantiomerically enriched epoxide of formula IIIa or IIIb to give, again, desired l-NBV and d-NBV.

In a preferred embodiment of the invention, the coupling reaction of a compound of formula IIa or IIb wherein R is a 6-fluoro-3,4-dihydro-1-benzopyran group and X is a —NHC(=O)OR$_1$ group and R$_1$ is defined above comprises the following steps.

An enantiomerically enriched compound of formula IIa or IIb is, separately, hydrolysed into the corresponding amino-alcohol in accordance with the following scheme

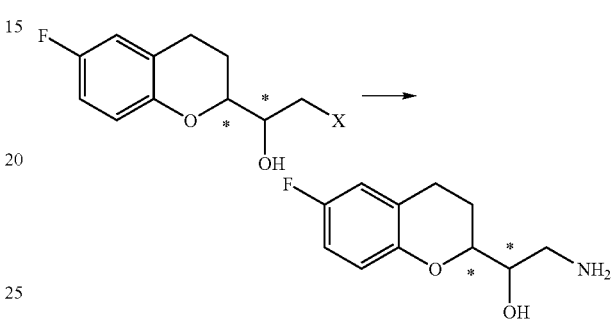

wherein X is —NHC(=O)OR$_1$ and R$_1$ is a ($C_1$-$C_4$)-alkyl or benzyl group; and so obtained enantiomerically enriched amino-alcohol is reacted with correspondent enantiomerically enriched epoxide of formula IIIa or IIIb to give desired l-NBV and d-NBV in accordance with known methods (Tetrahedron 2000, 56, 6339-6344).

The compounds of formula IIa or IIb and IIIa or IIIb wherein R is a 6-fluoro chromen-2-yl group or 6-fluoro-4-oxo-4H-1-benzopyran are converted in compounds of formula IIa or IIb and IIIa or IIIb wherein R is a 6-fluoro-3,4-dihydro-1-benzopyran group and, respectively, 6-fluoro-4-oxo-1-benzopyran group according to know techniques such as by reduction reaction.

As used herein, the symbols R and S show the absolute configuration at the asymmetric carbon atoms; a solid triangle represents a bond in the up configuration; a dashed triangle represents a bond in the down configuration; a wavy line denotes that the bond may be either in the up or in the down configuration and the asterisk means that the adjacent carbon atom is an asymmetric carbon atom.

The term "racemic mixture" refers to a compound in the form of a mixture of stereoisomers which are enantiomers. The term "diastereomeric mixture" refers to a compound in the form of a mixture of stereoisomers which are not enantiomers.

The term "non racemic" with regard to the chiral catalyst refers to a preparation of catalyst having greater than 50% of a given enantiomer, preferably at least 75%.

The abbreviation "Ph" as used herein represents the phenyl group. The abbreviation "Bn" as used herein represents the benzyl group. The abbreviation "Ts" as used herein represents the tosyl group.

The term "Bronsted acid" as used herein refers to any molecular entity which is capable of donating a proton.

The present invention develops a simple stereoselective route which allows to synthesize the single, active, NBV stereoisomers. According to the invention, the key chroman epoxides are separated into two diastereoisomers both in racemic mixture and, subsequently, converted into the four stereoisomers of said epoxide or correspondent amino alcohol derivatives.

A careful combination of said stereoisomers, in accordance with known techniques, leads only to the desired l-NBV and d-NBV forms.

There are several advantages in this synthesis.

The resolving agent is used in catalytic amount.

The resolution of the racemic epoxide by hydrolytic or aminolytic kinetic resolution of the invention is a very easy process because it only requires a filtration step to separate one enantiomer as an enantiomerically enriched 2-substituted alcohol of formula IIa or IIb, which precipitates from the reaction mixture, from the second enantiomer as an enantiomerically enriched epoxide of formula IIIa or IIb, which remains in the mother liquors.

The enantiomerically enriched epoxide of formula IIIa or IIIb, recovered from mother liquors, can be used without purification or, optionally, isolated as benzyl-amino alcohol derivative.

The hydrolytic or aminolytic kinetic resolution of the invention provides enantiomerically enriched 2-substituted alcohol of formula IIa or IIb and, respectively, enantiomerically enriched epoxide of the formula IIIa or IIIb endowed with very high optical purity (e.e. greater than 99%).

The whole process involves a lower number of steps than the previously described methods and allows avoiding the formation of undesired diastereoisomers of Nebivolol that would be wasted. In this way the overall efficiency of the process is greatly increased and as a consequence the manufacturing cost of the pharmaceutically active ingredient can, in principle, be lowered.

In fact, in accordance with the invention the epoxide racemic mixture A and B are only converted in chiral substrates which are entirely used in the preparation of NBV.

In other words, the process of the invention leads only to intermediates endowed with stereochemistry suitable to prepare desired l-NBV and d-NBV by avoiding loss in useful material.

A further aspect of the present invention refers to a compound of formula:

[(R)-2-((R)-6-fluoro-chroman-2-yl)-2-hydroxy-ethyl]-carbamic acid benzyl ester;
[(S)-2-((S)-6-fluoro-chroman-2-yl)-2-hydroxy-ethyl]-carbamic acid benzyl ester;
[(R)-2-((S)-6-fluoro-chroman-2-yl)-2-hydroxy-ethyl]-carbamic acid benzyl ester;
[(S)-2-((R)-6-fluoro-chroman-2-yl)-2-hydroxy-ethyl]-carbamic acid benzyl ester;

as useful intermediates in the preparation of d-NBV and l-NBV.

A further aspect of the present invention refers to the use of (S,S)—Co (salen) or (R,R)—Co (salen) catalysts in the resolution reaction of terminal epoxide of formula I.

A further aspect of the present invention refers to the use of (S,S)—Co (salen) and (R,R)—Co (salen) catalysts in the preparation of NBV.

A practical embodiment of the process object of the present invention comprises the optional separation of a compound of formula Ia into racemic mixture A and racemic mixture B; said racemic mixtures A and B are, separately, subjected to an aminolytic or hydrolytic kinetic resolution in the presence of a suitable non racemic transition metal-ligand catalyst complex preferably a non racemic (R,R or S,S) salen Co catalyst complex, to give an enantiomerically enriched substituted alcohol of formula IIa or IIb and, respectively an enantiomerically enriched epoxide of formula IIIa or IIIb; then, a substituted alcohol of formula IIa or IIb coming from the resolution of mixture A or mixture B is converted into corresponding epoxide or amino alcohol, wherein the stereochemistry is maintained, and reacted with an enantiomerically enriched epoxide of formula IIIa or IIIb coming from the resolution of mixture B or, respectively, mixture A or correspondent benzyl amino alcohol derivative thereof; the latter compounds are then converted in d-NBV or l-NBV or salts thereof in accordance with known methods.

It is to be understood that while the invention is described in conjunction of the preferred embodiments thereof, those skilled in the art are aware that other embodiments could be made without departing from the spirit of the invention.

For better illustrating the invention the following examples are now given.

EXAMPLE 1

Synthesis of (R)-1-((R)-6-fluoro-3,4-dihydro-2H-chromen-2-yl)-ethane-1,2-diol

The catalyst (R,R)-(−)-N,N'-Bis-(3,5-di-tert-butylsalicylidene)-1,2-cyclo-hexane-diamino-cobalt-(II) (29.6 mg) was dissolved in toluene (0.5 ml) and treated with 4-nitrobenzoic acid (16.5 mg). The solution was allowed to stir at rt open to air for 1 h over which time the colour changed from orange-red to dark brown.

To the solution of catalyst the (±)-[1S*(S*)]-6-fluoro-3,4-dihydro-2-(oxiran-2-yl)-2H-chromene (5.121 g) and MTBE (6 ml) were added and the mixture obtained was treated with $H_2O$ (0.237 g).

The reaction was left to stir at 25° C. for 3 h over which time the heterogeneous mixture was obtained.

The reaction was diluted with heptane (5 ml) and cooled to 0° C. After 2 h the solid was collected by vacuum filtration and rinsed with heptane/MTBE 1/1 (10 ml) to give the title diol as a white powder (2.47 g, HPLC purity: 99%, e.e. >99%).

NMR: $\delta_H$(400 MHz; $CDCl_3$) 6.82-6.73 (3H, m), 4.10-4.03 (1H, m), 3.89-3.75 (3H, m), 2.93-2.74 (2H, m), 2.65 (1H, b), 2.10 (1H, b), 2.04-1.90 (2H, m).

EXAMPLE 2

Synthesis of (R)-1-((S)-6-fluoro-3,4-dihydro-2H-chromen-2-yl)-ethane-1,2-diol

The catalyst (R,R)-(−)-N,N'-Bis-(3,5-di-tert-butylsalicylidene)-1,2-cyclo-hexane-diamino-cobalt-(II) (54.9 mg) was dissolved in toluene (2 ml) and treated with acetic acid (11 mg). The solution was allowed to stir at rt open to air for 1 h and was concentrated in vacuum to obtain a crude brown solid.

The resulting catalyst residue was dissolved in (±)-[1S*(R*)]-6-fluoro-3,4-dihydro-2-(oxiran-2-yl)-2H-chromene (1 g) and MTBE (2 ml) and the mixture obtained was treated with $H_2O$ (0.046 g).

The reaction was left to stir at 25° C. for 21 h over which time the heterogeneous mixture was obtained.

The reaction was cooled to 0° C. and after 1 h the solid was collected by vacuum filtration and rinsed with MTBE (2 ml) to give the title diol as a white powder (0.417 g, HPLC purity: 98%, e.e. >99%).

NMR: $\delta_H$(400 MHz; $CDCl_3$) 6.83-6.69 (3H, m, Ar), 4.05-3.98 (1H, m), 3.90-3.80 (3H, m), 2.91-2.74 (2H, m), 2.18-2.11 (1H, m), 1.91-1.81 (1H, m).

EXAMPLE 3

Synthesis of (S)-1-((R)-6-fluoro-3,4-dihydro-2H-chromen-2-yl)-ethane-1,2-diol

The catalyst (S,S)-(−)-N,N'-Bis-(3,5-di-tert-butylsalicylidene)-1,2-cyclo-hexane-diamino-cobalt-(II) (54.9 mg) was dissolved in toluene (2 ml) and treated with AcOH (11 mg). The solution was allowed to stir at rt open to air for 1 h and was concentrated in vacuo to obtain a crude brown solid.

The resulting catalyst residue was dissolved in (±)-[1S*(R*)]-6-fluoro-3,4-dihydro-2-(oxiran-2-yl)-2H-chromene (1 g) and MTBE (2 ml) and the mixture obtained was treated with $H_2O$ (0.046 g).

The reaction was left to stir at 25° C. for 21 h over which time the heterogeneous mixture was obtained.

The reaction was cooled to 0° C. and after 1 h the solid was collected by vacuum filtration and rinsed with MTBE (2 ml) to give the title diol as a white powder (0.417 g, HPLC purity: 98%, e.e. >99%).

NMR: $\delta_H$(400 MHz; $CDCl_3$) 6.83-6.69 (3H, m, Ar), 4.05-3.98 (1H, m), 3.90-3.80 (3H, m), 2.91-2.74 (2H, m), 2.18-2.11 (1H, m), 1.91-1.81 (1H, m).

EXAMPLE 4

Synthesis of (R)-1-((S)-6-fluoro-3,4-dihydro-2H-chromen-2-yl)-ethane-1,2-diol and of (S)-2-(benzylamino)-1-((R)-6-fluoro-3,4-dihydro-2H-chromen-2-yl)-ethanol Part A: the catalyst (R,R)-(−)-N,N'-Bis(3,5-di-tert-butylsalicylidene)-1,2-cyclo-hexane-diamino-cobalt-(II) (60 mg) was dissolved in toluene (5 ml) and treated with 4-nitrobenzoic acid (34.9 mg). The solution was allowed to stir at rt open to air for 1 h and was concentrated in vacuo to obtain a crude brown solid.

The resulting catalyst residue was dissolved in (±)-[1S*(R*)]-6-fluoro-3,4-dihydro-2-(oxiran-2-yl)-2H-chromene (4 g) and MTBE (4 ml) and the mixture obtained was treated with $H_2O$ (0.96 g).

The reaction was left to stir at 25° C. for 16 h over which time the heterogeneous mixture was obtained.

The reaction was diluted with heptane (4 ml) and cooled to 0° C. After 2 h the solid was collected by vacuum filtration and rinsed with heptane/MTBE 1/1 (4 ml) to give the title diol as a white powder (1.2 g, HPLC purity: 99%, e.e. >99%).

Part B: the filtrate was concentrated by rotary evaporation and ethanol (10 ml) and benzylamine (3.3 g) were added to the residue. The mixture was heated to 80° C. and after 2 h was concentrated in vacuum to obtain an oil residue. This was diluted with toluene (20 ml) and washed with $H_2O$ (3×20 ml). The organic phase was concentrated and the residue was purified by crystallization with ethanol to give the title benzylamino-alcohol as a white powder (1.4 g, HPLC purity: 94%, e.e. >99%).

NMR: $\delta_H$(400 MHz; $CDCl_3$) 7.37-7.27 (5H, m, Ar), 6.82-6.67 (3H, m, Ar), 3.9-3.7 (4H, m), 3.0-2.95 (1H, dd), 2.88-2.71 (3H, m), 2.18-2.09 (1H, m), 1.9-1.75 (1H, m).

EXAMPLE 5

Synthesis of (S)-1-((S)-6-fluoro-3,4-dihydro-2H-chromen-2-yl)-ethane-1,2-diol and of (R)-2-(benzylamino)-1-((R)-6-fluoro-3,4-dihydro-2H-chromen-2-yl)-ethanol Part A: the catalyst (S,S)-(+)-N,N'-Bis(3,5-di-tert-butylsalicylidene)-1,2-cyclo-hexane-diamino-cobalt-(II) (18.2 mg) was dissolved in toluene (3 ml) and treated with 4-nitrobenzoic acid (10.8 mg). The solution was allowed to stir at rt open to air for 1 h and was concentrated in vacuum to obtain a crude brown solid.

The resulting catalyst residue was dissolved in (±)-[1S*(S*)]-6-fluoro-3,4-dihydro-2-(oxiran-2-yl)-2H-chromene (3 g) and MTBE (4 ml) and the mixture obtained was treated with $H_2O$ (0.139 g).

The reaction was left to stir at 25° C. for 18 h over which time the heterogeneous mixture was obtained.

The reaction was diluted with heptane (8 ml) and cooled to 0° C. After 2 h the solid was collected by vacuum filtration and rinsed with heptane/MTBE 1/1 (2 ml) to give the title diol as a white powder (1.24 g, HPLC purity: 97.5%, e.e. >99%).

Part B: the filtrate was concentrated by rotary evaporation and the heptane/toluene 9/1 (10 ml) and benzylamine (2.48 g) were added to the residue. The mixture was heated to 80° C. and after 4 h was allowed to warm to rt and the solid was collected by vacuum filtration to give the title benzylamino-alcohol as a white powder (0.94 g, HPLC purity: 99%, e.e. >99%).

NMR: $\delta_H$(400 MHz; $CDCl_3$) 7.39-7.27 (5H, m, Ar), 6.82-6.67 (3H, m, Ar), 4.0-3.76 (4H, m), 3.97-2.7 (4H, m), 2.0-1.8 (2H, m).

EXAMPLE 6

Synthesis of [(R)-2-((R)-6-fluoro-chroman-2-yl)-2-hydroxy-ethyl]-carbamic acid benzyl ester The catalyst (R,R)-(−)-N,N'-Bis(3,5-di-tert-butylsalicylidene)-1,2-cyclo-hexane-diamino-cobalt-(II) (42 mg) was dissolved in MTBE (2 ml) and treated with 4-nitro-benzoic acid (22 mg). The solution was allowed to stir at rt open to air for 1 h over which time the colour changed from orange-red to dark brown.

To the solution of catalyst benzyl carbamate (116 mg) and MTBE (0.5 ml) were added and the mixture was stirred at rt for 0.5 h, then the (±)-[1S*(S*)]-6-fluoro-3,4-dihydro-2-(oxiran-2-yl)-2H-chromene (324 mg) and MTBE (1 ml) were added and stirring was continued over night.

An heterogeneous mixture was obtained and the solid was collected by vacuum filtration and rinsed with MTBE (1.5 ml) to give the title CBZ-amino-alcohol as a white powder (HPLC purity: 99%, e.e. >99%).

NMR: $\delta_H$(400 MHz; $CDCl_3$) 7.37-7.27 (5H, m, Ar), 6.82-6.72 (3H, m, Ar), 5.34 (1H, sb), 5.10 (2H, s), 3.93-3.87 (1H, ddd), 3.85-3.75 (1H, m), 3.55-3.37 (2H, m), 2.9-2.7 (3H, m), 2.1-2.0 (1H, m), 1.95-1.80 (1H, m)

EXAMPLE 7

Synthesis of [(S)-2-((S)-6-fluoro-chroman-2-yl)-2-hydroxy-ethyl]-carbamic acid benzyl ester The catalyst (S,S)-(+)-N,N'-Bis(3,5-di-tert-butylsalicylidene)-1,2-cyclo-hexane-diamino-cobalt-(II) (14.5 mg) was dissolved in toluene (1 ml) and treated with 4-nitrobenzoic acid (8 mg). The solution was allowed to stir at rt open to air for 1 h and was concentrated in vacuum to obtain a crude brown solid.

To the resulting catalyst residue benzyl carbamate (97 mg), MTBE (0.5 ml) and (±)-[1S*(S*)]-6-fluoro-3,4-dihydro-2-(oxiran-2-yl)-2H-chromene (250 mg) were added and the mixture was stirred at rt over night.

An heterogeneous mixture was obtained and the solid was collected by vacuum filtration and rinsed with MTBE to give the title CBZ-amino-alcohol as a white powder (HPLC purity: 99%, e.e. >99%).

EXAMPLE 8

Synthesis of [(S)-2-((R)-6-fluoro-chroman-2-yl)-2-hydroxy-ethyl]-carbamic acid benzyl ester The catalyst (S,S)-(+)-N,N'-Bis-(3,5-di-tert-butylsalicylidene)-1,2-cyclo-hexane-diamino-cobalt-(II) (58 mg) was dissolved in dichloromethane (3.0 ml) and treated with 4-nitro-benzoic acid (35 mg). The solution was allowed to stir at rt open to air for 1 h over which time the colour changed from orange-red to dark brown and then was concentrated in vacuo to obtain a crude brown solid.

To the resulting catalyst residue benzyl carbamate (176 mg), MTBE (0.5 ml) and (±)-[1S*(R*)]-6-fluoro-3,4-dihydro-2-(oxiran-2-yl)-2H-chromene (450 mg) were added and the mixture was stirred at rt over night.

An heterogeneous mixture was obtained and the solid was collected by vacuum filtration and rinsed with MTBE to give the title CBZ-amino-alcohol as a white powder (112 mg, HPLC purity: 99%, e.e. >99%).

NMR: $\delta_H$(400 MHz; CDCl$_3$) 7.42-7.32 (5H, m, Ar), 6.84-6.70 (3H, m, Ar), 5.25 (1H, sb), 5.14 (2H, s), 3.97-3.91 (1H, m), 3.87-3.81 (1H, m), 3.74-3.65 (1H, m), 3.44-3.34 (1H, m), 2.91-2.74 (2H, m), 2.25-2.15 (1H, m), 1.90-1.78 (1H, m)

EXAMPLE 9

Synthesis of [(R)-2-((S)-6-fluoro-chroman-2-yl)-2-hydroxy-ethyl]-carbamic acid benzyl ester The catalyst (R,R)-(+)-N,N'-Bis-(3,5-di-tert-butylsalicylidene)-1,2-cyclo-hexane-diamino-cobalt-(II) (29 mg) was dissolved in dichloromethane (1.5 ml) and treated with 4-nitro-benzoic acid (16 mg). The solution was allowed to stir at rt open to air for 1 h over which time the colour changed from orange-red to dark brown and then was concentrated in vacuo to obtain a crude brown solid.

To the resulting catalyst residue benzyl carbamate (175 mg), MTBE (0.5 ml) and (±)-[1S*(R*)]-6-fluoro-3,4-dihydro-2-(oxiran-2-yl)-2H-chromene (450 mg) were added and the mixture was stirred at rt over night.

An heterogeneous mixture was obtained and the solid was collected by vacuum filtration and rinsed with MTBE to give the title CBZ-amino-alcohol as a white powder (HPLC purity: 99%, e.e. >99%).

EXAMPLE 10

Synthesis of 2-amino-1-[6-fluoro-(2R)-3H,4H-2-2chromenyl]-(1R)-ethan-1-ol

To a solution of [(R)-2-((R)-6-fluoro-chroman-2-yl)-2-hydroxy-ethyl]-carbamic acid benzyl ester (0.250 g) in dry methanol (5 ml) at room temperature was added 10% Pd-charcoal (8 mg) and stirred under hydrogen atmosphere (3 bar).

After 8 h the reaction mixture was filtered and the filtrate was concentrated under vacuum to give the title compound (0.14 g) as an oil.

EXAMPLE 11

Synthesis of 2-amino-1-[6-fluoro-(2R)-3H,4H-2-2chromenyl]-(1S)-ethan-1-ol

To a solution of [(S)-2-((R)-6-fluoro-chroman-2-yl)-2-hydroxy-ethyl]-carbamic acid benzyl ester (0.250 g) in dry methanol (5 ml) at room temperature was added 10% Pd-charcoal (8 mg) and stirred under hydrogen atmosphere (3 bar).

After 8 h the reaction mixture was filtered and the filtrate was concentrated under vacuum to give the title compound (0.14 g) as an oil.

EXAMPLE 12

Synthesis of (−)-(R,S,S,S)-α,α'-imino-bis-(methylene)-bis-(6-fluoro-3,4-dihydro-2H,1-benzopyran-2-methanol)-hydrochloride The mother liquor obtained in Example 6 was concentrated by rotary evaporation and the residue was dissolved in dry t-butanol (5 ml). 2-amino-1-[6-fluoro-(2R)-3H,4H-2-2chromenyl]-(1S)-ethan-1-ol and a catalytic amount of BF$_3$.O(Et)$_2$ were added and the resulting mixture was refluxed for 4 h.

The solvent was removed under vacuum and washed with brine and extracted with ethyl acetate and dried over Na$_2$SO$_4$. The volatiles were concentrated and the residue dissolved in EtOH and dry HCl gas was passed through the solution to form the title hydrochloride salt.

NMP: $\delta_H$(400 MHz; CD$_3$OD) 6.84-6.74 (6H, m), 4.12-3.89 (4H, m), 3.52-3.18 (4H, m), 2.96-2.77 (4H, m), 2.28-2.20 (1H, m), 2.05-1.86 (2H, m), 1.83-1.72 (1H, m).

EXAMPLE 13

Synthesis of (+)-(S,R,R,R)-α,α'-imino-bis-(methylene)-bis-(6-fluoro-3,4-dihydro-2H,1-benzopyran-2-methanol)-hydrochloride The mother liquor obtained in Example 8 was concentrated by rotary evaporation and the residue was dissolved in dry t-butanol (5 ml). 2-amino-1-[6-fluoro-(2R)-3H,4H-2-2chromenyl]-(1R)-ethan-1-ol and a catalytic amount of BF$_3$.O(Et)$_2$ were added and the resulting mixture was refluxed for 4 h.

The solvent was removed under vacuum and washed with brine and extracted with ethyl acetate and dried over Na$_2$SO$_4$. The volatiles were concentrated and the residue dissolved in EtOH and dry HCl gas was passed through the solution to form the title hydrochloride salt.

NMR: $\delta_H$(400 MHz; CD$_3$OD) 6.84-6.74 (6H, m), 4.12-3.89 (4H, m), 3.52-3.18 (4H, m), 2.96-2.77 (4H, m), 2.28-2.20 (1H, m), 2.05-1.86 (2H, m), 1.83-1.72 (1H, m).

EXAMPLE 14

Synthesis of (S)-1-((R)-6-fluoro-3,4-dihydro-2H-chromen-2-yl)-ethane-1,2-diol and of (R)-2-(benzylamino)-1-((R)-6-fluoro-3,4-dihydro-2H-chromen-2-yl)-ethanol Part A: the catalyst (S,S)-(−)-N,N'-Bis-(3,5-di-tert-butylsalicylidene)-1,2-cyclo-hexane-diamino-cobalt-(II) (12.0 mg) was dissolved in toluene (0.1 ml) and treated with AcOH (6.6 mg). The solution was allowed to stir at rt open to air for 1 h and was concentrated in vacuo to obtain a crude brown solid.

The resulting catalyst residue was dissolved in (2R)-6-fluoro-2-[(2S)-oxiran-2-yl]-3,4-dihydro-2H-chromene (0.97 g), (2R)-6-fluoro-2-[(2R)-oxiran-2-yl]-3,4-dihydro-2H-chromene (0.97 g) [(R,R)-,(R,S)-epoxide diastereoisomeric mixture)] and MTBE (2.36 ml) and the mixture obtained was treated with $H_2O$ (0.099 g).

The reaction was left to stir at 25° C. for 24 h over which time the heterogeneous mixture was obtained.

The reaction was cooled to 5° C. and after 1 h the solid was collected by vacuum filtration and rinsed with MTBE (2.8 ml) to give the title diol as a white powder (0.613 g, HPLC purity: 97.7%, e.e. >99%).

Part B: the filtrate was treated according to experimental procedure described in Example 5, Part. B, to give the title benzylamino-alcohol as a white powder.

NMR: $\delta_H$(400 MHz; $CDCl_3$) 6.83-6.69 (3H, m, Ar), 4.05-3.98 (1H, m), 3.90-3.80 (3H, m), 2.91-2.74 (2H, m), 2.18-2.11 (1H, m), 1.91-1.81 (1H, m).

NMR: $\delta_H$(400 MHz; $CDCl_3$) 7.39-7.27 (5H, m, Ar), 6.82-6.67 (3H, m, Ar), 4.0-3.76 (4H, m), 3.97-2.7 (4H, m), 2.0-1.8 (2H, m).

EXAMPLE 15

Synthesis of (R)-1-((S)-6-fluoro-3,4-dihydro-2H-chromen-2-yl)-ethane-1,2-diol and of (S)-2-(benzylamino)-1-((S)-6-fluoro-3,4-dihydro-2H-chromen-2-yl)-ethanol By working according to experimental procedure described in Example 14 but in the presence of (R,R)-(−)-N,N'-Bis(3,5-di-tert-butylsalicylidene)-1,2-cyclo-hexane-diamino-cobalt-(II) catalyst, a hydrolytic kinetic resolution was carried out on the (S,R)-,(S,S)-epoxide diastereoisomeric mixture to give the title diol and benzylamino-alcohol compounds as white powders.

The invention claimed is:

1. A process for the separation of a racemic terminal epoxide of formula

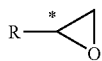
(I)

wherein R is a group of formula

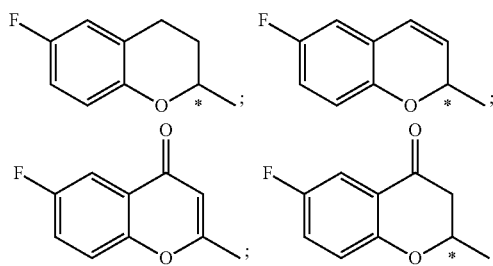

said process comprising carrying out a hydrolytic or aminolytic kinetic resolution of a racemic terminal epoxide of formula (I) in the presence of a non-racemic transition metal-ligand catalyst complex to give an enantiomerically enriched substituted alcohol of formula

(IIa)

(IIb)

wherein X is hydroxy or amino;
and, respectively, an enantiomerically enriched epoxide of formula

(IIIa)

(IIIb)

2. A process according to claim 1 wherein the ligand is a chiral salen ligand.

3. A process according to claim 1 wherein the transition metal is Co.

4. A process according to claim 1 wherein non-racemic transition metal-ligand catalyst complex is a Co-(salen) catalyst complex.

5. A process according to claim 4 wherein non-racemic catalyst complex is (S,S)—Co(II) (salen) catalyst or (R,R)—Co(II) (salen) catalyst.

6. A process according to claim 4 wherein non-racemic catalyst complex is selected from (S,S)—Co(III)-(salen)-(p-nitro-benzoate), (R,R)—Co(III)-(salen)-(p-nitro-benzoate), (S,S)—Co(III)-(salen)-(acetate) and (R,R)—Co(III)-(salen)-(acetate).

7. A process according to claim 1 wherein the amount of catalyst complex is comprised from 0.01 to 10 mol % with regard to a compound of formula I.

8. A process according to claim 7 wherein said amount is comprised from 0.01 to 5 mol %.

9. A process according to claim 8 wherein said amount is comprised from 0.05 to 1 mol %.

10. A process according to claim 1 wherein said hydrolytic or aminolytic kinetic resolution comprises contacting a nucleophile and a racemic or diastereoisomeric mixture of a compound of formula I in the presence of a non-racemic transition metal-ligand catalyst complex.

11. A process according to claim 10 wherein contacting step is carried out at a temperature comprised between about −10° C. and about 50° C.

12. A process according to claim 11 wherein contacting step is carried out at around room temperature.

13. A process according to claim 10 wherein said nucleophile is water, hydroxide, acetate, benzoate, formate, chloroformate, carbamate, azide or imide.

14. A process according to claim 13 wherein said nucleophile is water.

15. A process according to claim 13 wherein said nucleophile is benzyl carbamate.

16. A process according to claim 10 wherein said kinetic resolution comprises:

a) dissolution of a catalyst complex in a suitable aprotic or protic solvent;
b) activation of a catalyst complex by reaction with a suitable oxidizing agent in the presence of an organic or inorganic acid;
c) contacting the active catalyst complex with a racemic or diastereoisomeric mixture of a compound of formula I and a suitable nucleophile; and
d) filtering the reaction mixture.

17. A process according to claim 10 wherein said kinetic resolution comprises:
a') contacting an oxidizing agent with a mixture comprising a racemic or diastereoisomeric compound of formula I, a non racemic catalyst complex, an organic or inorganic acid and a suitable nucleophile; and
b') filtrating the reaction mixture.

18. A process according to claim 16 wherein the oxidizing agent is oxygen.

19. A process according to claim 18 wherein oxygen is introduced in the form of air.

20. A process according to claim 16 wherein in the activation of the catalyst complex organic Bronsted acids are used.

21. A process for the separation of racemic terminal epoxide of formula

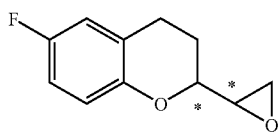

(Ia)

to give an enantiomerically enriched substituted alcohol of formula

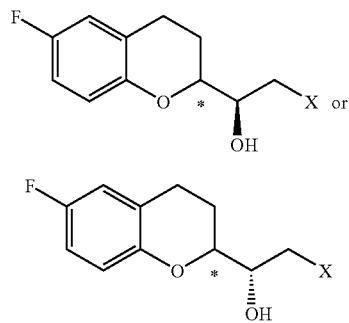

wherein X is defined above;
and, respectively, an enantiomerically enriched epoxide of formula

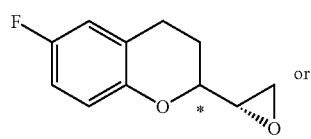

(IIIa)

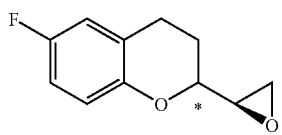

(IIIb)

which comprises a hydrolytic or aminolytic kinetic resolution carried out in the presence of a non-racemic transition metal-ligand catalyst complex.

22. A process according to claim 21 wherein said hydrolytic or aminolytic kinetic resolution is carried out on partially resolved compounds of formula Ia

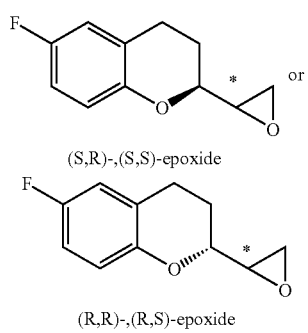

(S,R)-,(S,S)-epoxide (R,R)-,(R,S)-epoxide in the form of diastereoisomeric mixtures.

23. A process according to claim 21 wherein said hydrolytic or aminolytic kinetic resolution is carried out on partially resolved compounds of formula Ia

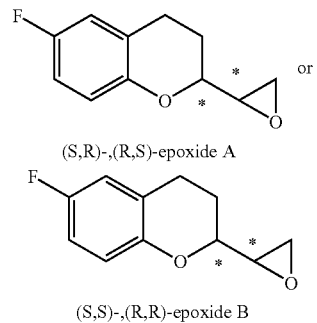

(S,R)-,(R,S)-epoxide A (S,S)-,(R,R)-epoxide B in the form of racemic mixtures.

24. A process according to claim 23 further comprising the partial resolution of the four stereoisomers of formula Ia into two racemic mixtures.

25. A process for preparing Nebivolol which comprises the separation of racemic terminal epoxide according to claim 1.

26. A compound of formula:
[(R)-2-((R)-6-fluoro-chroman-2-yl)-2-hydroxy-ethyl]-carbamic acid benzyl ester;
[(S)-2-((S)-6-fluoro-chroman-2-yl)-2-hydroxy-ethyl]-carbamic acid benzyl ester;
[(R)-2-((S)-6-fluoro-chroman-2-yl)-2-hydroxy-ethyl]-carbamic acid benzyl ester;
[(S)-2-((R)-6-fluoro-chroman-2-yl)-2-hydroxy-ethyl]-carbamic acid benzyl ester.

27. The process of claim 25, wherein said non-racemic transition metal-ligand catalyst complex is (S,S)—Co (salen) catalyst or (R,R)—Co (salen) catalyst.

* * * * *